(12) United States Patent
Irion et al.

(10) Patent No.: US 6,640,131 B1
(45) Date of Patent: Oct. 28, 2003

(54) DEVICE FOR PHOTODYNAMIC DIAGNOSIS OR TREATMENT

(75) Inventors: Klaus M. Irion, Liptingen (DE); Herbert Stepp, Planegg (DE); Andre Erhardt, Tuttlingen (DE); Hans Tafelmaier, Rosenheim (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/242,709

(22) PCT Filed: Apr. 2, 1998

(86) PCT No.: PCT/DE98/00937

§ 371 (c)(1),
(2), (4) Date: Mar. 14, 2001

(87) PCT Pub. No.: WO98/43534

PCT Pub. Date: Oct. 8, 1998

(30) Foreign Application Priority Data

Apr. 2, 1997 (DE) .......................... 197 15 320
May 22, 1997 (DE) .......................... 197 21 454

(51) Int. Cl.⁷ .............................................. A61B 5/00
(52) U.S. Cl. .................... 600/476; 600/109; 600/178; 607/88

(58) Field of Search .................. 600/407, 476–478, 600/109, 160, 178, 182, 431; 607/88

(56) References Cited

U.S. PATENT DOCUMENTS 4,056,724 A * 11/1977 Harte .......................... 250/328

FOREIGN PATENT DOCUMENTS

| DE | 4133493 A1 | * | 4/1992 |
| DE | 19646176 A1 | * | 5/1997 |
| EP | 241268 A2 | * | 10/1987 |

* cited by examiner

Primary Examiner—Ruth S. Smith
(74) Attorney, Agent, or Firm—St. Onge Steward Johnson & Reens LLC

(57) ABSTRACT

An endoscopic or microscopic apparatus for diagnosis by means of a light-induced reaction in biologic tissue "in vivo" which is created by a photo-amboceptor or by autofluorescence is provided. The inventive apparatus is characterized by the feature that at least one reference wavelength $\lambda_r$ is provided which is longer by up to $2\Delta\lambda$ at maximum or smaller than the wavelength $\lambda_s$ at the point of intersection.

28 Claims, 5 Drawing Sheets

DEVICE FOR PHOTODYNAMIC DIAGNOSIS OR TREATMENT

FIELD OF THE INVENTION

The present invention relates to an apparatus for the "in vivo" diagnosis by means of a light-induced reaction created by an endogenous or exogenous photo-amboceptor.

In order to trigger a light-induced reaction in biologic systems a photo-amboceptor is administered to the patient in a concentration of a few mg/kg body weight.

PRIOR ART

Typical photo-amboceptors or sensitisers are Photofrin or Photosan, which present a basic hemato-porphyrin framework structure, protoporphyrin IX induced by δ-aminolaevulic acid (ALA) (PPIX), which has been used in urology and dermatology for a short time, 9-Oac-tetramethoxy porphycene, benzoporphyrin derivatives, as-partyl chlorine $E_6$, m-tetrahydroxyphenyl chlorine, Sn(IV) etiopurpurine or Zn(II) phthalocyanine.

These substances accumulate in tumour tissues in a concentration increased by roughly two to fifteen times. This selective concentration in tumour tissue is the decisive basis of the photodynamic diaghosis (PDD) and photodynamic therapy (PDT).

For diagnosis the tissue to be analysed is irradiated after an appropriate waiting period following the administration of the photo-amboceptor, with blue or violet light—in known devices with laser light almost exclusively. The photo-amboceptor, which is present in an increased concentration in tumour tissue, is excited by this light and displays in response a typical red fluorescence by which the tumour can be localized.

Apart from fluorescence—which is produced by a photo-amboceptor accumulated in the tissue—the so-called autofluorescence of the tissue may be triggered, too, which is brought about by endogenous fluorescent pigments. In this case mostly blue or ultraviolet light is used for excitation as well.

In dependence on the respective photo-amboceptors used, the photodynamic diagnosis (PDD) entails certain problems. When photofrin and photosan-3 are used as photo-amboceptors in photodynamic diagnosis highly complex engineering devices are required for the detection of fluorescence because, on account of interfering autofluorescence fractions, only very complex computer-assisted image processing techniques and highly sensitive cameras with residual-light intensifier are suitable for an appropriate detection of the fluorescence in tumor tissue.

When δ-aminolaevulic acid (ALA) is used the induced fluorescence is strong enough for recognition merely by visual inspection.

However, the fluorescence achieved by means of δ-aminolaevulic acid does not furnish an optimum quality of the image which is to be recorded as part of the diagnosis. This is due, inter alia, to variabilities of the optical tissue parameters which take an influence on the fluorescent intensity in a non-specific manner.

It is moreover known to use photo-amboceptors for photodynamic therapy (PDT). In this respect reference is made to the document WO 93/20810, which is, by the way, also referred to explicitly with respect to the explanation of all terms and steps of operation which are not described here in more details.

The devices used for photodynamic diagnosis—which is also referred to as fluorescent diagnosis—or for photodynamic therapy, respectively, which are also termed "PDD" or "PDT" devices, comprise an illuminating system, a light-feeding unit which directs the light from the illuminating unit to the tissue region to be diagnosed and/or treated, and an imaging, an image-recording and possibly an image-transmitting unit which images the light coming from the tissue region into a proximal image plane.

The illuminating system and the light-supplying unit define the path of the illuminating beam whilst the imaging, the image-recording and possibly the image-transmitting unit define the path of the observation beam.

In an endoscopic PDD device the light-supplying unit consists of the light guide, which connects the illuminating system to the light guide connector of the endoscope, for instance, and the illuminating light guide of the endoscope. The light guide may be a quartz light guide or a fluid light guide, for instance. Fluid or quartz light guides offer a better transmission in the blue or violet range than standard glass light guides. The endoscope lens, which is disposed on the distal end and covers the tissue range illuminated by the light emerging from the illuminating light guide, constitutes the image-recording unit; the image of the lens is picked up, for instance, by means of one or several CCD receivers which serve as opto-electronic image converter unit. When the CCD receiver is disposed on the proximal end the lens image is transmitted by a relay lens system or an imaging fiber bundle which hence fulfill the function of the image-transmitting unit.

In the PCT application PCT/DE 96/01831, which is not a prior publication, it has been proposed to perform endoscopic photodynamic diagnosis and therapy by means of an apparatus in which a "source of white light" is used as light source rather than a laser, i.e. a light source which generates incoherent light in the wavelength range of at least from 390 to 650 nm. The light from the light source is fed via a focusing unit into the fiber optic light guide.

The aforementioned application contains moreover the proposal to harmonize the spectral internal transmittance factor or the (spectral) transmission function, respectively, of the light-feeding unit with the spectral internal transmittance factor or the (spectral function), respectively, of the imaging or image-recording unit in such a way that only a fraction of the light reflected on the irradiated tissue contributes to the production of the image, which is so dimensioned that the fluorescent image will not be glared or blanketed by this "background picture".

Filter systems are used, as a rule, to set the transmission function. The filter systems so far proposed entail the disadvantage, however, that small errors due to tolerances are sufficient to result in major variations of the reflected light quantity which contributes to the production of the image, which errors occur particularly in terms of the edge position and the steepness of the transmission edge. This effect, in its turn, results in a major change of the ratio between the fluorescent light and the background light.

When, for instance, the filter graph of the filter system introduced into the path of the illuminating beam is shifted towards shorter wavelengths as a result of manufacturing or assembly faults—tilting of the filter, etc.—the overlapping of the transmission zones of the filter systems introduced into the paths of the illuminating and observation beams is practically reduced to "zero" in the event of small shifts already so that a background image is not obtained as a result of the directly reflected light and only a fluorescent image is achieved.

Vice versa, with a small shift towards longer wavelengths already an excessive overlapping is achieved so that the fluorescent image is blanketed by the visible ("non"-fluorescent) background picture.

Moreover, a variation of the steepness of the transmission edge also displaces the position of the transmission graph in the lower transmission range so that this error requires compensation like an edge position error. In the upper range the overall transmission is, as a matter of fact, subjected only to a slight change.

Similar problems occur also in devices where a photodynamic diagnosis is performed by means of a microscope and particularly a surgical microscope. Appropriate devices are described in the European Patent EP 0 241 268 A1 or the U.S. Pat. No. 5,371,624.

The problems which may occur in filter selection are described also in the U.S. Pat. No. 4,056,724—cf. FIG. 14 in particular.

In all other respects explicit reference is made to these prior art documents as far as the explanation of all terms is concerned which are not described here in details.

BRIEF DESCRIPTION OF THE INVENTION

The present invention is based on the problem of proposing a spectral internal transmittance characteristic or a transmission function for the path of the illuminating beam and/or the path of the observation beam, in which tolerance-induced errors, particularly in terms of the edge position and the steepness of the transmission edges, produce distinctly lower effects than other systems as far as the ratio between the light quantities of the fluorescent light and the directly reflected light is concerned which contributes to the production of the image.

Inventive solutions to this problem are defined in Patent Claim 1. Improvements of the invention are the subject matters of Claims 2 to 9. The Claims 10 and 11 relate to filters for use in a PDD apparatus.

The invention is based on the fundamental idea of designing the transmission graphs in such a way that at least one of the transmission graphs presents a section having a "flat slope" so that edge position and edge steepness errors take only a slight influence on the overall transmission. With this provision the effect is achieved that the overall transmission, which is achieved by a convolution of the transmission of the path of the illuminating beam with the transmission of the path of the observation beam and by integration over the relevant wavelength range, will be influenced only slightly by the displacement of the edge position and/or the steepness of the transmission edge.

In accordance with the invention therefore the spectral internal transmittance or the spectral transmission function $T_1(\lambda)$, respectively, of the light-feeding unit or the path of the illuminating beam is therefore matched with the fluorescence excitation spectrum of the photo-amboceptor or of the tissue, respectively, and the spectral internal transmittance or the spectral transmission function $T_b(\lambda)$, respectively, of the imaging unit or of the path of the observation beam, respectively, with the fluorescence spectrum of the photo-amboceptor or the tissue, respectively. Moreover, the transmission function $T_1(\lambda)$ of the path of the illuminating beam intersects the transmission function $T_b(\lambda)$ of the path of the observation beam at a transmission value not exceeding 30%.

The invention starts out from the basic idea that the transmittance levels or the spectral transmission functions, respectively, of the paths of the illuminating and observation beams intersect in a zone where at least one transmittance graph presents a flat slope—at least in the event of averaging or substitution of the actual graph by a straight line over a wavelength range from 10 to 30 nm—so that a displacement of one or of both graphs entails only a comparatively slight variation of the area enclosed by the two graphs.

To this end it is decisive that there is at least one reference wavelength $\lambda_r$, which is longer by $2\Delta\lambda_s$ at maximum or shorter than the wavelength $\lambda_s$ at the point of intersection, for which hence applies $$\lambda_s - 2\Delta\lambda \leq \lambda_r \leq \lambda_s + 2\Delta\lambda$$

and starting out from which the spectral transmission function $T_1(\lambda)$ of the path of the illuminating beam satisfies the following conditions for at least five wavelengths $\lambda_r$, $\lambda_r + \Delta\lambda$, $\lambda_r + 3\Delta\lambda$, $\lambda_r - \Delta\lambda$, and $\lambda_r - 2\Delta\lambda$:

| | |
|---|---|
| $\|T_1(\lambda_r - \Delta\lambda) - T_1(\lambda_r - 2\Delta\lambda)\|$ | >10% |
| $\|T_1(\lambda_r + \Delta\lambda) + T_1(\lambda_r + 3\Delta\lambda)\|$ | <5%, preferably <3% |
| $T_1(\lambda_r)$ | >0.5% |
| $T_1(\lambda_r - \Delta\lambda)$ | >0.5% |
| $T_1(\lambda_r - 2\Delta\lambda)$ | >0.5% |
| $T_1(\lambda_r + \Delta\lambda)$ | >0.3% |
| $T_1(\lambda_r + 3\Delta\lambda)$ | >0.3% | wherein $$4 \text{ nm} < \Delta\lambda < 6 \text{ nm}$$

and/or the spectral transmission function $T_b(\lambda)$ of the path of the observation beam satisfies the following conditions for at least five wavelengths $\lambda_r$, $\lambda_r - \Delta\lambda$, $\lambda_r - 3\Delta\lambda$, $\lambda_r + \Delta\lambda$, and $\lambda_r + 2\Delta\lambda$:

| | |
|---|---|
| $\|T_b(\lambda_r + \Delta\lambda) - T_b(\lambda_r + 2\Delta\lambda)\|$ | >10% |
| $\|T_b(\lambda_r - \Delta\lambda) - T_b(\lambda_r - 3\Delta\lambda)\|$ | <5%, preferably <3% |
| $T_b(\lambda_r)$ | >0.5% |
| $T_b(\lambda_r + \Delta\lambda)$ | >0.5% |
| $T_b(\lambda_r + 2\Delta\lambda)$ | >0.5% |
| $T_b(\lambda_r - \Delta\lambda)$ | >0.3% |
| $T_b(\lambda_r - 3\Delta\lambda)$ | >0.3% | wherein $$4 \text{ nm} < \Delta\lambda < 6 \text{ nm}.$$

The transmission functions in the light-feeding and the image-producing section of the inventive apparatus are so selected that only a precisely set light quantity of the illuminating light, which is reflected on the tissue and has naturally a comparatively high intensity, "arrives" through the imaging apparatus section in the proximal image plane whereas light having a wavelength $\lambda$ can arrive from the zone where fluorescence occurs in the proximal image plane only if it comes from the illuminated tissue region rather than from the illuminating system.

The inventively selected transmission functions of the path of the illuminating beam and of the path of the observation beam of the apparatus ensure that the illuminated tissue region is so strongly irradiated with light of a wavelength which is not within the range of the fluorescence spectrum, so that the examining person can perceive details of the illuminated tissue region independently of the fluorescent radiation on account of the light directly reflected in this wavelength region, which furnishes a background picture.

In other terms, in accordance with the invention the image of the tissue region illuminated with exciting light is produced simultaneously by means of fluorescent light and reflected illuminating light, with the two fractions, which contribute both to the production of the image, being so set in terms of their wavelength and with respect to their intensity that they will not "interfere" with each other.

It is preferable to have the setting made in such a way that the intensity of the emitted fluorescent light is within the same order as the overall intensity of the reflected fraction of the exciting light of the illuminating system—weighted by the filter characteristic of the observation system. In a particularly expedient form the setting is made such that the two intensities are roughly the same.

It is moreover expedient that the two spectral transmittances intersect at a value less than 10%, preferably at a value less than 5%.

In an improvement of the invention the transmission function of the path of the illuminating beam has an almost horizontal plateau or a local maximum within the range $\lambda_r \ldots \lambda_r+3\Delta\lambda$ and/or the transmission function of the path of the observation beam has an almost horizontal plateau or a local maximum within the range $\lambda_r \ldots \lambda_r-3\Delta\lambda$.

When an ALA-induced PPIX has been selected as photo-amboceptor it is preferable that the spectral transmittance of the path of the illuminating beam satisfies the following relationship $$100\% > T_1(\lambda)400 \ldots 420) \leq 80\%$$

$$15\% > T_1(\lambda)440 \ldots 455) \leq 0.5\%.$$

With this configuration of the spectral transmission function of the light-feeding unit and the imaging unit the effect is achieved that the fluorescent light may be clearly perceived with a high contrast on the image of the vicinity of a tumour, for instance, which is produced by the illuminating light.

For an adaptation to the various photo-amboceptors and/or different diagnostic conditions or for a conversion of the inventive apparatus to a therapeutic technique it is moreover preferred that the transmission properties of the light-transmitting and the imaging units can be adjusted by means of one or several optical elements.

The optical elements which are used to set the transmission functions of the light-transmitting and the imaging units are preferably filter systems such as absorption filters, interference filters or even prisms as well as electrically controllable LC filters (liquid crystal filters) which are adapted for being introduced into the paths of the illuminating and observation beams. In this set-up the expression "path of the illuminating beam" is understood to denote the optical path from the lamp of the light source to the light-feeding unit, through this unit and from this unit to the tissue region under diagnosis. The optical elements and particularly the filter systems may be arranged, on principle, at any point of this optical path, preferably at points where the optical path is parallel. However, the arrangement between the illuminating system and the light-feeding unit, i.e. ahead of a light guide fiber bundle, for instance, is particularly preferable. In the description of the filter system or systems the internal transmittance of the respective optical path without filter system is assumed to be 100%.

By way of analogy, the expression "path of the observation beam" is understood to denote the optical path from the illuminated tissue region to the imaging unit and from this unit to proximal image plane. (without a filter system here, too, the internal transmittance is assumed to be 100%.) A fine adjustment of the transmission graphs of the paths of the illuminating or observation beam may be effected by means of supplementary tilting of the filter elements.

When the inventive apparatus is integrated into an endoscope the image plane in the endoscope may be located both in the region of the distal end—e.g. when a video chip is used which is disposed on the distal end—and in the region of the proximal end. In the latter case the path of the observation beam includes, in addition to a lens as image-receiving optical unit, a relay lens system or a flexible fiber bundle, for instance, as image-transmitting unit. When a relay lens system or a fiber bundle is employed as image-transmitting unit the filter systems introduced into the path of the observation beam are preferably disposed between the "last flat" of the relay lens system or the exit facet of the fiber bundle, respectively, and the proximal image plane.

When the inventive apparatus is integrated into a surgical microscope the microscope lens system is an element of the imaging unit, which may be followed, for instance, by a video pickup as electronic image-recording unit.

The color filters of the video chip are disregarded in the filter characteristic. Further filters, which are possibly provided in the optical path, must, however, also be considered in the determination of the internal transmittance.

In another embodiment of the invention the filter, which may be introduced into the path of the illuminating beam, includes at least two separate filters whereof one is a thermoresistant interference filter unit whilst the other one is a thermoresistant heat-absorbing filter. The thermoresistant interference filter unit, in its turn, consists preferably of a short-pass and a blocking filter, which are disposed on separate substrates. This leads to distinctly improved transmission properties.

In one exemplary embodiment such a filter for use in the path of the illuminating beam of a PDD device, specifically when ALA-induced PPIX is used as photo-amboceptor, presents a spectral transmission function $T_1(\lambda)$ which satisfies the following conditions for at least five wavelengths $\lambda_r$, $\lambda_r+\Delta\lambda$, $\lambda_r+3\Delta\lambda$, $\lambda_r-\Delta\lambda$, and $\lambda_r-2\Delta\lambda$:

| | |
|---|---|
| $\|T_1(\lambda_r - \Delta\lambda) - T_1(\lambda_r - 2\Delta\lambda)\|$ | >10% |
| $\|T_1(\lambda_r + \Delta\lambda) + T_1(\lambda_r + 3\Delta\lambda)\|$ | <5%, preferably <3% |
| $T_1(\lambda_r)$ | >0.5% |
| $T_1(\lambda_r - \Delta\lambda)$ | >0.5% |
| $T_1(\lambda_r - 2\Delta\lambda)$ | >0.5% |
| $T_1(\lambda_r + \Delta\lambda)$ | >0.3% |
| $T_1(\lambda_r + 3\Delta\lambda)$ | >0.3% | wherein $$4 \text{ nm} < \Delta\lambda < 6 \text{ nm},$$

with $\lambda_r$ representing a reference wavelength which is selected as a function of the respectively used photo-amboceptor or the respective autofluorescence, respectively, and for which applies, for instance, when ALA is used as photo-amboceptor:

$$438 \text{ nm} - 2\Delta\lambda \leq \lambda_r \leq 438 \text{ nm} + 2\Delta\lambda.$$

In another exemplary embodiment such a filter for use in the path of the observation beam in a PDD apparatus, particularly when ALA-induced PPIX is used as photo-amboceptor, has a spectral transmission function $T_1(\lambda)$ which satisfies the following conditions for at least five wavelengths $\lambda_r$, $\lambda_r-\Delta\lambda$, $\lambda_r-3\Delta\lambda$, $\lambda_r+\Delta\lambda$, and $\lambda_r+2\Delta\lambda$:

| | |
|---|---|
| $\|T_b(\lambda_r + \Delta\lambda) - T_b(\lambda_r + 2\Delta\lambda)\|$ | >10% |
| $\|T_b(\lambda_r - \Delta\lambda) - T_b(\lambda_r - 3\Delta\lambda)\|$ | <5%, preferably <3% |
| $T_b(\lambda_r)$ | >0.5% |
| $T_b(\lambda_r + \Delta\lambda)$ | >0.5% |
| $T_b(\lambda_r + 2\Delta\lambda)$ | >0.5% |
| $T_b(\lambda_r - \Delta\lambda)$ | >0.3% |
| $T_b(\lambda_r - 3\Delta\lambda)$ | >0.3% | wherein $$4\text{ nm} < \Delta\lambda < 6\text{ nm},$$

with $\lambda_r$ representing a reference wavelength which is selected as a function of the respectively used photo-amboceptor or the respective autofluorescence, respectively, and for which applies, for instance, when ALA-induced PPIX is used as photo-amboceptor:

$$438\text{ nm} - 2\Delta\lambda \leq \lambda_r \leq 438\text{ nm} + 2\Delta\lambda.$$

The filter may be an interference filter in particular, having quartz or a heat-resistant glass such as "Schoft Borofloat" as a substrate material.

When another photo-amboceptor is used the filter properties must be appropriately adapted:

The use of optical elements and filters in particular for taking an influence of the transmission characteristic or transmission function, respectively, of the optical path presents the advantage that a normal white-light illumination and observation may be performed, for instance when the filters are tilted out of the path so that the examiner such as a surgeon can assess the tissue region examined by a fluorescence diagnosis, inter alia by the color. The color is an essential criterion of assessment in the field of ophthalmology, for instance.

Common light sources, and specifically light sources known from endoscopy, may be used as light sources, too, which emit wide-band light over the aforementioned wavelength range. Such a light source which emits light with a sufficient intensity is, for example, a gas discharge lamp and a xenon discharge tube in particular. If in an isolated case the luminous efficacy of the light source should be insufficient it is possible to use a "pulsed" light source such as a flash device with a flash lamp or even a laser in addition to a "continuously operating" light source.

BRIEF DESCRIPTION OF THE DRAWING

The invention will be described in the following in more details with reference to the drawing wherein.

DESCRIPTION OF AN EMBODIMENT

Figure 1:
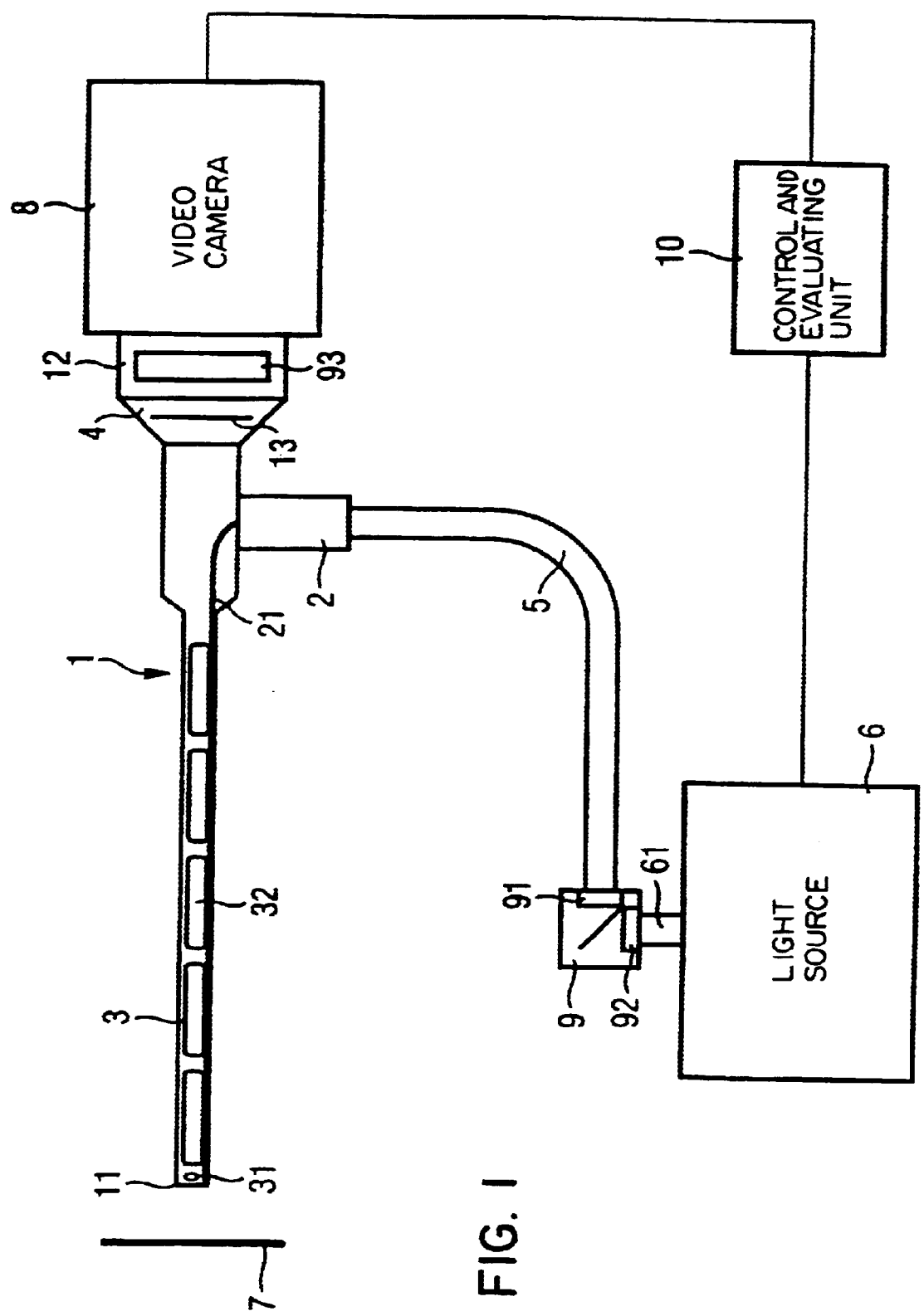
FIG. 1 is a schematic view of an inventive apparatus for endoscopic applications.

FIG. 1 is a schematic view of an embodiment of an inventive apparatus for endoscopic applications. The reference numeral 1 designates an endoscope which comprises, in a manner known per se, a light-guide connector 2, a rod-shaped element 3 for introduction into a human body (which is not illustrated here) and an eyepiece 4.

The light guide connector 2 is connected to a light source 6 via a fiber optic light guide 5, which light source may include, for instance, a xenon discharge tube. A light guide 21 in the endoscope, which may consist of a fiber bundle, for example, passes the light of the light source 6, which is fed into the light guide connector 2, to the distal end 11 of the endoscope. The light emerging from the distal end 11 illuminates the tissue region 7 to be examined.

The light arriving from the tissue region 7 enters a lens 31 of the endoscope 1, which is illustrated in a schematic form only. The image produced by the lens 31 is guided by an image-relaying section 32, which may include relay lens systems including rod-shaped lenses or a fibre imaging system, to the proximal end 12 of the endoscope. The image of the tissue region 7, which is produced in the proximal image plane 13, may be viewed with the eye through the eyepiece. The image may be shot with a video camera 8 alternatively or, via a beam splitter, in addition, for viewing with the eye. FIG. 1 shows the alternative that the video camera 8 is attached directly on the eyepiece 4.

As far as described above, the structure is known, for instance, from the endoscopes equipped with a video camera, which are manufactured by Karl Storz GmbH & Co., Tuttlingen, Germany. Regarding details of the structure therefore reference is made to the known endoscopes of this manufacturer.

Filter systems may be inserted into the path of the illuminating beam and the path of the observation beam so as to perform a so-called photodynamic diagnosis.

To this end, a filter system 9 is mounted on the light output terminal 61 of the light source 6 in the embodiment illustrated in FIG. 1, with the fiber optic light guide 5 being flange-mounted on the filter system. The filter system 9 comprises a thermoresistant interference filter 91 and a thermoresistant heat-absorbing filter 92 which is intended to reduce the thermal load on the interference filter 91 substantially. A filter 93 is mounted ahead of the video camera 8, too.

The exposure setting of the video camera 8 and the light emission from the light source 6 are controlled by a control and evaluating unit 10. The control and evaluating unit 10 may, for instance, be suitable to synchronise a photoflash source with the light integration phase of a CCD chip in the video camera 8. Moreover, the control and evaluating unit 10 may control the luminous power emitted from the light source 6 and/or the exposure setting of the video camera.

Furthermore, the output signal of the video camera 8 is applied to the control and evaluating unit 10. The evaluating unit may comprise, in particular, an image processing system which processes the video camera output signal in the manner described by way of introduction and which displays the image-processed output signal on a monitor. The output signal directly output by the video camera and/or image-processed may, of course, also be stored in a device such as a recorder and/or in an image data base or processed further in any other way by means of electronic data processing systems.

When a photo-amboceptor is used the tissue region 7 emits both reflected illuminating light and fluorescent light which is created by the light-induced reaction in biologic systems, which is created by the photo-amboceptor. In order to be able to detect the fraction of fluorescent light, which is small compared to the reflected fraction, and to distinguish it reliably from the "non-fluorescent light" in the subsequent image processing step an appropriately selected transmission characteristic of the paths of the illuminating and the observation beams is required. For setting the transmission characteristic during the photodynamic diagnosis the filters 91 and 93 are provided which may be introduced into the optical path. As the filters may be removed again, e.g. by tilting them out of the optical paths, a normal observation of the tissue region 7 is possible, too, without any risk of effects, such as color distortion.

Figure 2:
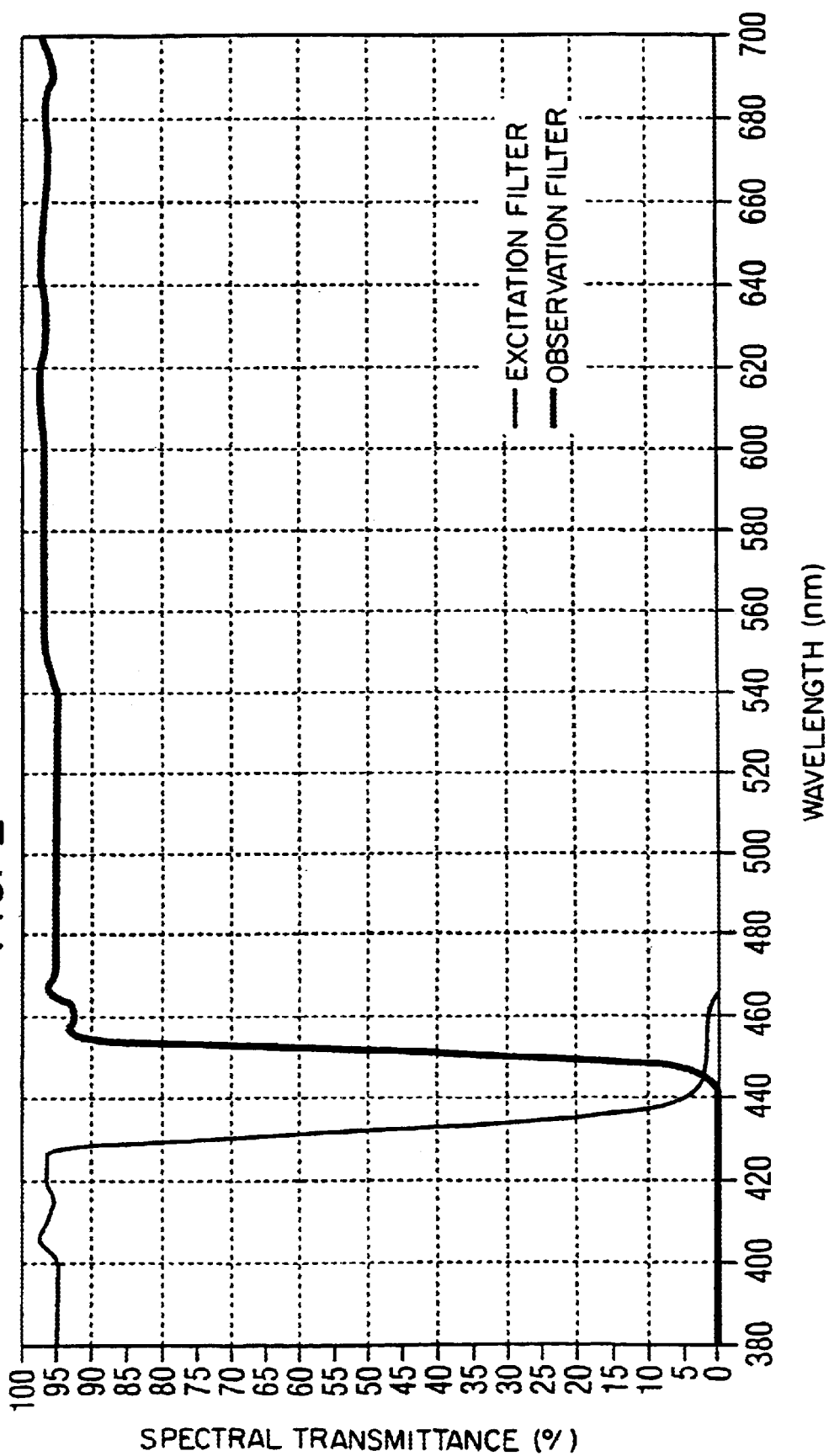
FIG. 2 is a schematic representation of the filter characteristic of an embodiment.

With reference to FIG. 2 how the characteristic of the filters 91 and 93 will be explained in the following. In these figures the characteristics of the filters in the path of the illuminating beam (excitation filter) and in the observation beam (observation filter) are described for one embodiment with reference to the case that δ-aminolaevuic acid is used as photo-amboceptor. When other photo-amboceptors are used the filter characteristic must be adapted correspondingly.

Regarding the numerical values of the transmission values or the spectral transmittance $T(\lambda)$ (in %) as a function of the wavelength $\lambda$ reference is made explicitly to these Figures.

Figure 3:
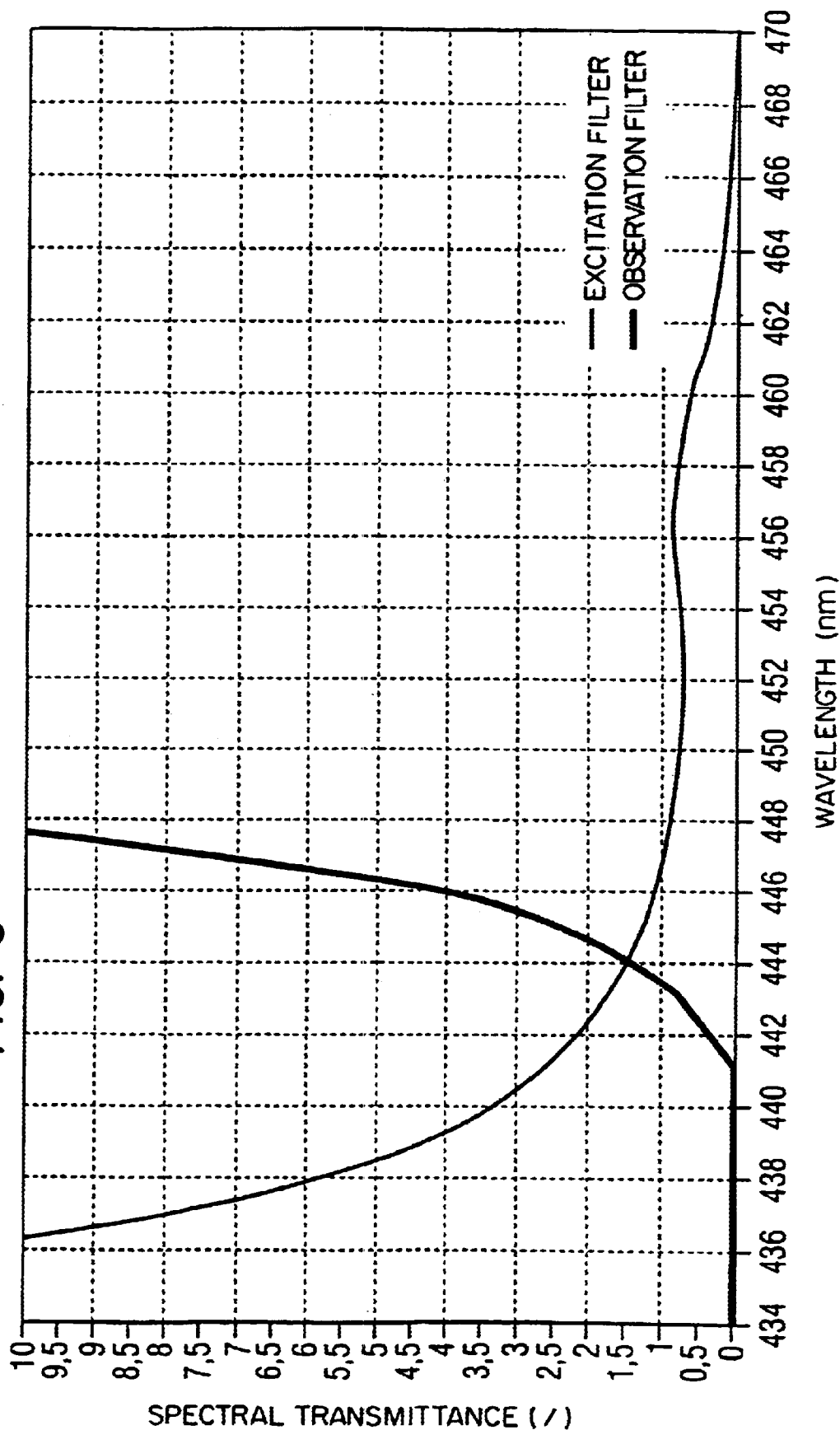
FIG. 3 is an enlarged view of the region where the two filter curves intersect.

It is apparent from FIG. 2 that the transmission of the excitation filter presents a steep drop towards longer wavelengths from approximately 425 nm onwards. By contrast to the filter characteristic described in the PCT application PCT/DE96/01831, the transmission at wavelengths longer than roughly 450 nm is practically not zero but exceeds rather 0.5 & over a range of at least 10 nm, however it is smaller than 5% (cf. FIG. 3).

This flat run-out over a major wavelength range of the transmission graph of the excitation filter substantially determines the overlapping of the two transmission graphs, i.e. the quantity of the transmitted light which the observer perceives as "background picture" in addition to the induced fluorescent light.

A displacement of one of the two graphs as a result of manufacturing faults etc. hence takes a substantially smaller influence on the transmitted quantity of light than is the case in prior art.

Figure 4A:
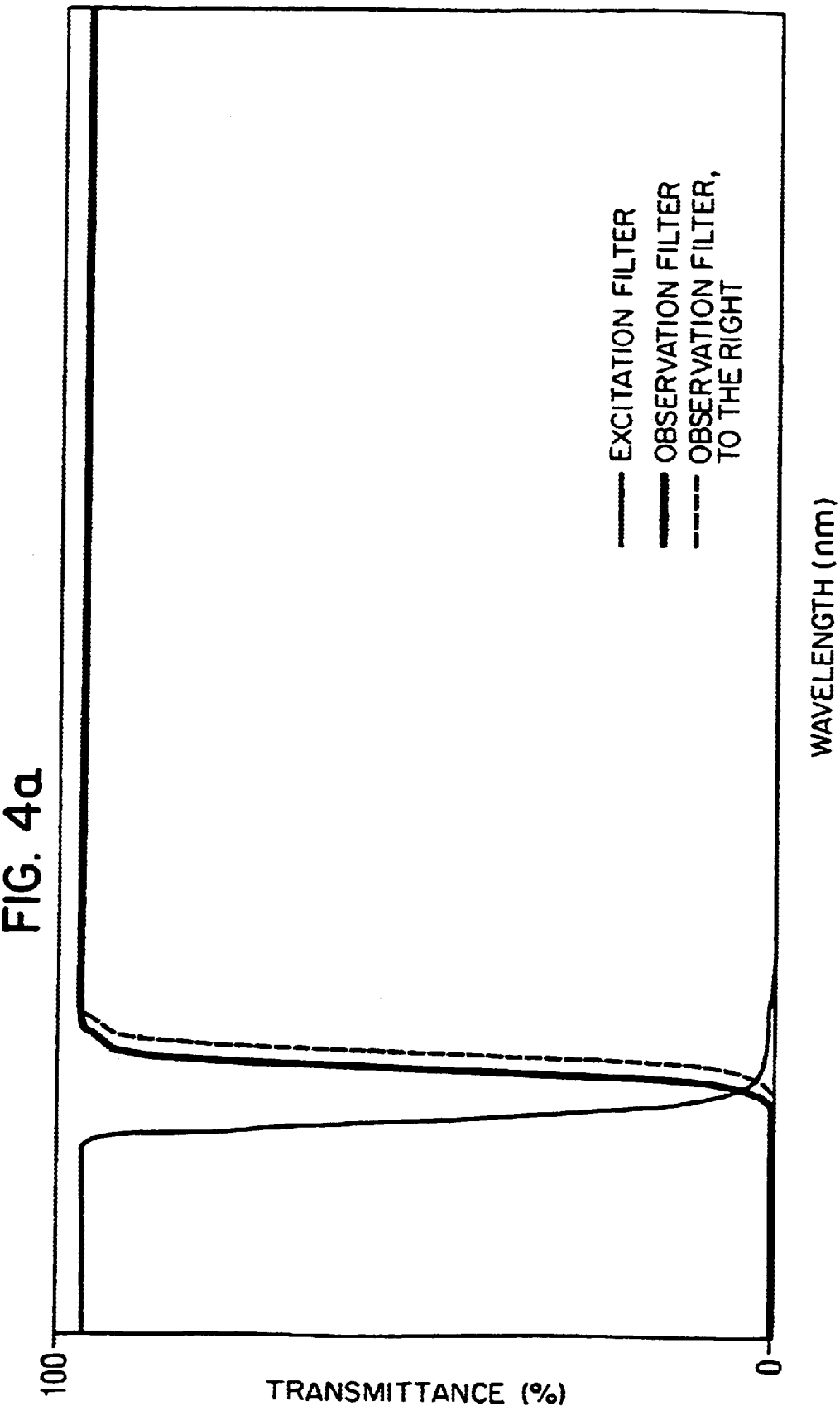
FIG. 4a is an illustration for explaining the advantages of the invention.

This is illustrated by FIG. 4a where, in addition to the desirable characteristic of the observation filter, an "actual characteristic" is indicated in dashed lines which is due to manufacturing faults and in which the filter graph is shifted by a defined wave length $\lambda$. As is apparent from FIG. 4b the fault takes only a slight influence on the transmitted quantity of light.

Figure 4B:
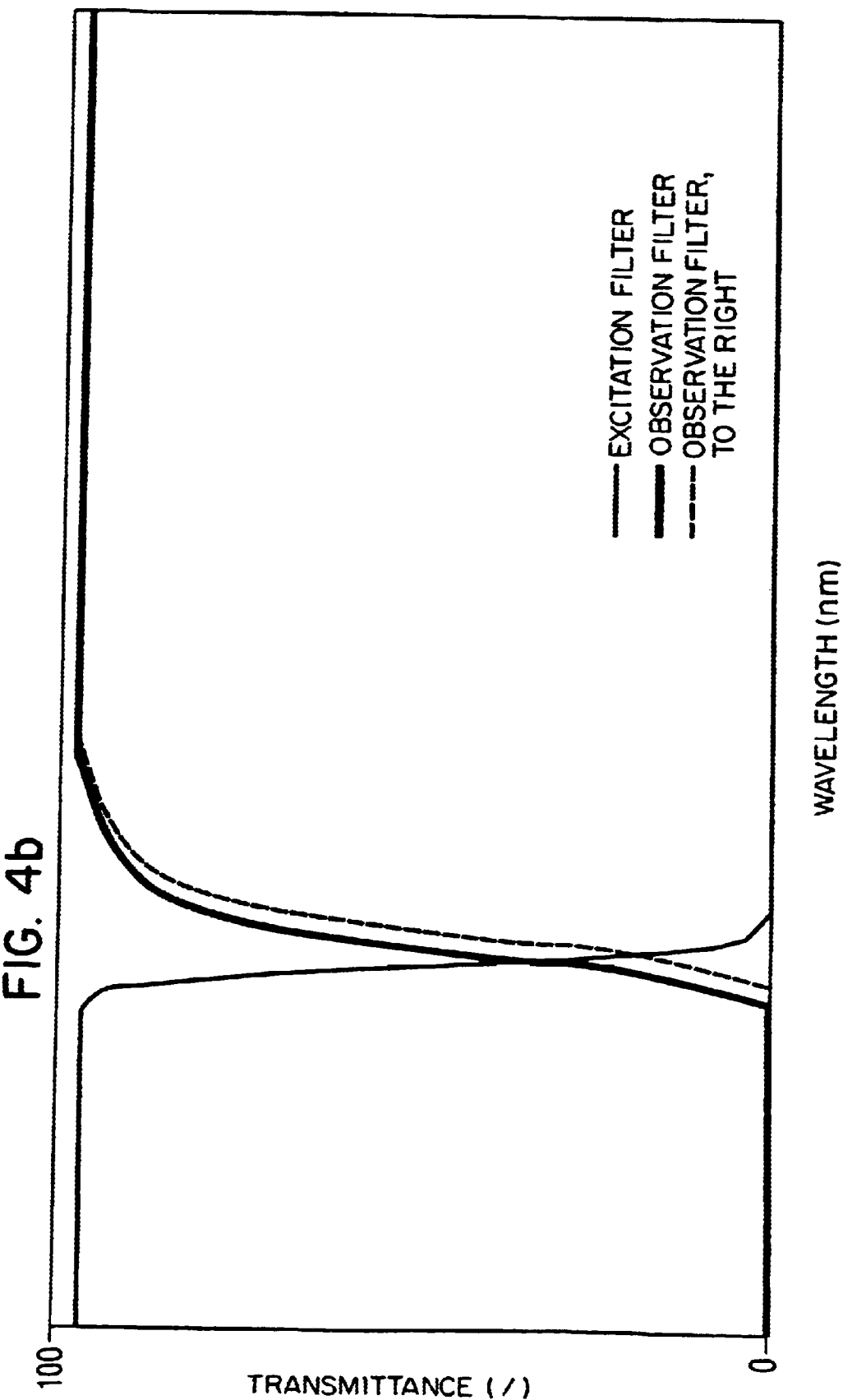
FIG. 4b is an illustration for explaining the disadvantages of prior art.

For comparison, FIG. 4b shows the variation occurring in prior art where the transmission of the excitation filter does not present an inventive plateau but drops to zero directly. With the shift of the transmissions by the of light which contributes to the background picture is reduced substantially more strongly than in the invention.

What is claimed is:

1. A system for diagnosis or therapeutic treatment by means of a light-induced reaction created in biologic tissue "in vivo", comprising
   a path of an illuminating beam constituted by
      at least one light source with a lamp system generating incoherent light in a wavelength range of at least 400 to 650 nm, and a light-feeding unit which directs the light of the at least one light source onto a tissue region to be diagnosed or therapeutically treated, presenting a spectral transmission function $T_1(\lambda)$ matched with the fluorescence excitation spectrum of the light-induced reaction and
   a path of an observation beam constituted by an imaging unit which images the light coming from said tissue region into an image plane, presenting a spectral transmission function $T_b(\lambda)$ matched with the fluorescence spectrum of the light-induced reaction wherein said spectral transmission function $T_1(\lambda)$ of said path of the illuminating beam and said spectral transmission function $T_b(\lambda)$ of said path of the observation beam intersect at wavelength $\lambda_s$ at which the transmission value of each optical path is not higher than 30%, wherein at least one reference wavelength $\lambda_r$ is provided which is longer by up to $2\Delta\lambda$ at maximum or smaller than the wavelength $\lambda_s$ at the point of intersection, for which hence applies:

$$\lambda_s - 2\Delta\lambda \leq \lambda_r \leq \lambda_s + 2\Delta\lambda$$

and starting out from which
the spectral transmission function $T_1(\lambda)$ of the path of the illuminating beam satisfies the following conditions for at least five wavelengths $\lambda_r$, $\lambda_r+\Delta\lambda$, $\lambda_r+3\Delta\lambda$, $\lambda_r-\Delta\lambda$, and $\lambda_r-2\Delta\lambda$:

$$|T_1(\lambda_r - \Delta\lambda) - T_1(\lambda_r - 2\Delta\lambda)| > 10\%$$
$$|T_1(\lambda_r + \Delta\lambda) + T_1(\lambda_r + 3\Delta\lambda)| < 5\%$$
$$T_1(\lambda_r) > 0.5\%$$
$$T_1(\lambda_r - \Delta\lambda) > 0.5\%$$
$$T_1(\lambda_r - 2\Delta\lambda) > 0.5\%$$
$$T_1(\lambda_r + \Delta\lambda) > 0.5\%$$
$$T_1(\lambda_r + 3\Delta\lambda) > 0.3\%$$

wherein
4 nm$<\Delta\lambda<$6 nm.

2. System according to claim 1, wherein said reference wavelength $\lambda_r$ equals the wavelength $\lambda_s$ at the point of intersection.

3. System according to claim 1, wherein said two transmission functions $T_1(\lambda)$ and $T_b(\lambda)$ intersect at a transmission value less than 10%.

4. System according claim 1, wherein said spectral transmission function $T_1(\lambda)$ of said path of the illuminating beam presents an almost horizontal plateau within the range $\lambda_r$ . . . $\lambda_r+3\Delta\lambda$.

5. System according to claim 1, wherein said spectral transmission function $T_1(\lambda)$ of said path of the illuminating beam presents a local maximum within the range $\lambda_r$ . . . $\lambda_r+3\Delta\lambda$.

6. System according to claim 1, wherein the spectral transmission function of said light feeding unit and said imaging unit are variable by means of one or several optical elements.

7. System according to claim 6, wherein said optical elements are interference filters.

8. System according to claim 1, wherein the spectral transmission functions are so set that the overall intensity of induced fluorescent light is within the same order as the overall intensity of a light fraction of the illuminating system, which is reflected directly on the tissue region.

9. System according to claim 1 wherein said imaging unit comprises an imager and an image recording unit.

10. System according to claim 1 wherein said imaging unit comprises an imager and an image-transmitting unit.

11. System according to claim 1, wherein said two transmission functions $T_1(\lambda)$ and $T_b(\lambda)$ intersect at a transmission value less than 5%.

12. System according to claim 1, wherein the light-induced reaction is created by a photo-amboceptor.

13. System according to claim 12, wherein when ALA is used as a photo-amboceptor said spectral transmission function $T_1(\lambda)$ of said path of the illuminating beam satisfies the following relationship:

$$100\% > T_1(\lambda)\ 400\ldots 420) \geq 80\%$$

$$15\% > T_1(\lambda)\ 440\ldots 455) \geq 0.5\%.$$

14. System according to claim 1, wherein the light-induced reaction is created by autofluorescence.

15. A system for diagnosis or therapeutic treatment by means of a light-induced reaction in biologic tissue "in vivo", comprising
   a path of an illuminating beam constituted by
      at least one light source with a lamp system generating incoherent light in a wavelength range of at least 400 to 650 nm, and a light-feeding unit which directs the light of the at least one light source onto a tissue region to be diagnosed or therapeutically treated, presenting a spectral transmission function $T_1(\lambda)$ matched with the fluorescence excitation spectrum of the light-induced reaction, and
   a path of an observation beam constituted by an imaging unit which images the light coming from said tissue region into an image plane, presenting a spectral transmission function $T_b(\lambda)$ matched with the fluorescence spectrum of the light-induced reaction wherein said spectral transmission function $T_1(\lambda)$ of said path of the illuminating beam and said spectral transmission function $T_b(\lambda)$ of said path of the observation beam intersect at wavelength $\lambda_s$ at which the transmission value of each optical path is not higher than 30%, wherein at least one reference wavelength $\lambda_r$ is provided which is longer by up to $2\Delta\lambda$ at maximum or smaller than the wavelength $\lambda_s$ at the point of intersection, for which hence applies:

$$\lambda_s - 2\Delta\lambda \leq \lambda_r \leq \lambda_s + 2\Delta\lambda$$

and starting out from which
   the spectral transmission function $T_b(\lambda)$ of the path of the observation beam satisfies the following conditions for at least five wavelengths $\lambda_r, \lambda_r - \Delta\lambda, \lambda_r - 3\Delta\lambda, \lambda_r + \Delta\lambda$, and $\lambda_r + 2\Delta\lambda$:

| | |
|---|---|
| $\|T_b(\lambda_r + \Delta\lambda) - T_b(\lambda_r + 2\Delta\lambda)\| >$ | 10% |
| $\|T_b(\lambda_r - \Delta\lambda) - T_b(\lambda_r - 3\Delta\lambda)\| <$ | 5% |
| $T_b(\lambda_r) >$ | 0.5% |
| $T_b(\lambda_r + \Delta\lambda) >$ | 0.5% |
| $T_b(\lambda_r + 2\Delta\lambda) >$ | 0.5% |
| $T_b(\lambda_r - \Delta\lambda) >$ | 0.3% |
| $T_b(\lambda_r - 3\Delta\lambda) >$ | 0.3% | wherein
   $4\ \text{nm} < \Delta\lambda < 6\ \text{nm}$.

16. System according to claim 15, wherein said reference wavelength $\lambda_r$ equals the wavelength $\lambda_s$ at the point of intersection.

17. System according to claim 15, wherein said two transmission functions $T_1(\lambda)$ and $T_b(\lambda)$ intersect at a transmission value less than 10%.

18. System according claim 15, wherein said spectral transmission function $T_b(\lambda)$ of said path of the observation beam has an almost horizontal plateau within the range $\lambda_r \ldots \lambda_r - 3\Delta\lambda$.

19. System according to claim 15, wherein said spectral transmission function $T_b(\lambda)$ of said path of the observation beam presents a local maximum within the range $\lambda_r \ldots \lambda_r - 3\Delta\lambda$.

20. System according to claim 15, wherein the spectral transmission function of said light feeding unit and said imaging unit are variable by means of one or several optical elements.

21. System according to claim 20, wherein said optical elements are interference filters.

22. System according to claim 15, wherein the spectral transmission functions are so set that the overall intensity of induced fluorescent light is within the same order as the overall intensity of a light fraction of the illuminating system, which is reflected directly on the tissue region.

23. System according to claim 15 wherein said imaging unit comprises an imager and an image recording unit.

24. System according to claim 15 wherein said imaging unit comprises an imager and an image-transmitting unit.

25. System according to claim 15, wherein said two transmission functions $T_1(\lambda)$ and $T_b(\lambda)$ intersect at a transmission value less than 5%.

26. System according to claim 15, wherein the light-induced reaction is created by a photo-amboceptor.

27. System according to claim 26, wherein when ALA is used as a photo-amboceptor said spectral transmission function $T_1(\lambda)$ of said path of the illuminating beam satisfies the following relationship:

$$100\% > T_1(\lambda)\ 400\ldots 420) \geq 80\%$$

$$15\% > T_1(\lambda)\ 440\ldots 455) \geq 0.5\%.$$

28. System according to claim 15, wherein the light-induced reaction is created by autofluorescence.

* * * * *